(12) United States Patent
Hoffman

(10) Patent No.: US 7,046,763 B2
(45) Date of Patent: May 16, 2006

(54) FIELD AND FACTORY TESTABLE IMAGING DETECTOR

(75) Inventor: David M. Hoffman, New Berlin, WI (US)

(73) Assignee: General Electric Company, Schnectady, NY (US)

( * ) Notice: Subject to any disclaimer, the term of this patent is extended or adjusted under 35 U.S.C. 154(b) by 181 days.

(21) Appl. No.: 10/707,604

(22) Filed: Dec. 23, 2003

(65) Prior Publication Data

US 2005/0135552 A1   Jun. 23, 2005

(51) Int. Cl.
 *H05G 1/64* (2006.01)
(52) U.S. Cl. .................. 378/98.8; 378/207; 250/252.1
(58) Field of Classification Search .................. 378/19, 378/207, 98.8; 250/368, 369, 370.11, 252.1, 250/363.09, 370.09, 591
See application file for complete search history.

(56) References Cited

U.S. PATENT DOCUMENTS

| | | | | |
|---|---|---|---|---|
| 4,047,034 A | * | 9/1977 | Auphan | .................. 250/354.1 |
| 5,565,678 A | * | 10/1996 | Manian | .................... 250/252.1 |
| 5,698,858 A | * | 12/1997 | Borner | ..................... 250/484.2 |
| 6,539,076 B1 | * | 3/2003 | Shoji | ......................... 378/98.8 |
| 6,658,082 B1 | * | 12/2003 | Okumura et al. | ............. 378/19 |
| 6,693,291 B1 | * | 2/2004 | Nelson et al. | ........... 250/505.1 |
| 2004/0113088 A1 | * | 6/2004 | Brabec et al. | ......... 250/370.11 |
| 2005/0111613 A1 | * | 5/2005 | Miner et al. | .................. 378/19 |

* cited by examiner

Primary Examiner—Edward J. Glick
Assistant Examiner—Anastasia Midkiff
(74) Attorney, Agent, or Firm—Michael DellaPenna

(57) ABSTRACT

An imaging assembly is provided including an x-ray source and a controller in communication with the x-ray source. A detector assembly is in communication with the controller, and includes a photodetector array in communication with the controller. A scintillator assembly is positioned between the photodetector array and the x-ray source. A collimator assembly is positioned in between the scintillator assembly and the x-ray source. An electroluminescent panel is positioned between the collimator assembly and the scintillator assembly. The electroluminescent panel is in communication with the controller and has an active condition where the electroluminescent panel generates radiation eliciting a response from the detector array.

21 Claims, 3 Drawing Sheets

FIELD AND FACTORY TESTABLE IMAGING DETECTOR

BACKGROUND OF INVENTION

The present invention relates generally to an imaging detector assembly, and, more particularly to a field testable imaging detector assembly for use in computed tomography applications.

Computed tomography has been utilized for a wide variety of imaging applications. One such category of applications is comprised of medical imaging. Although it is known that computed tomography may take on a wide variety of configurations within the medical industry, it commonly is based on the transmission of low energy rays through a body structure. These low energy rays are subsequently received and processed to formulate an image, often three-dimensional, of the body structure that can by analyzed by clinicians as a diagnostic aid.

The reception of the low energy rays, such as gamma rays or x-rays, is often accomplished through the use of a device referred to as a detector assembly. The detector assembly is typically comprised of a plurality of structures working in concert to receive and process the incoming energy rays after they have passed through the body structure. A collimator is an element often found in a detector assembly that is used to limit the direction of photons as they approach the scintillator element. The collimator is commonly used to control resolution or field of view. Their primary purpose, in a detector assembly, however, is to control the photons impinging on the scintillator element.

The scintillator element, in turn, is commonly a material with the ability to absorb the photons and convert their energy into visible light. This allows the low energy rays received by the scintillator detector to be converted into useful information. Scintillator elements may come in a wide variety of forms and may be adapted to receive a wide variety of incoming rays. The light produced by the scintillator element is commonly processed by way of a device such as a light sensitive photodiode which converts the light from the scintillator element into an amplified electronic signal. In this fashion, the information from the scintillator detector can be easily transferred, converted, and processed by electronic modules to facilitate viewing and manipulation by clinicians.

Finally detector assemblies are currently tested using x-ray excitation. In such tests x-rays are directed at the detector assembly to produce a response that can be evaluated. X-ray source equipment in field installed imaging systems, however, is often not suitable for proper detector testing procedures. It is often impossible, within field installed imaging systems, for an x-ray source to target specific regions of the detector assembly in order to properly run diagnostic procedures. Safety considerations, for example, prevent the remote triggering of x-rays from a remote location such as a manufacturers test of field equipment. Furthermore, prior to installation into the imaging system, an x-ray source may not even be available to test the detector assembly. Recalibration during a scan series in third generation CT systems is not available using existing detector assemblies since the patient may be blocking all or a portion of the detector assembly. In such situations, the patient is commonly required to be removed from the imaging system in order for recalibration to be effectuated. This increases scan-time, expense, and complexity of operation of existing imaging systems.

It would, however, be highly desirable to have a detector assembly that was suitable for field-testing without the need for x-ray generation. Similarly, it would be highly desirable to have an imaging system with a detector assembly that had characteristics that allowed recalibration without patient removal from the imaging system.

SUMMARY OF INVENTION

An imaging assembly is provided including an x-ray source and a controller in communication with the x-ray source. A detector assembly is in communication with the controller, and includes a detector array in communication with the controller. A scintillator assembly is positioned between the detector array and the x-ray source. A collimator assembly is positioned in between the scintillator assembly and the x-ray source. An electroluminescent panel is positioned between the collimator assembly and the scintillator assembly. The electroluminescent panel is in communication with the controller and has an active condition where the electroluminescent panel generates radiation eliciting a response from the detector array.

Other features of the present invention will become apparent when viewed in light of the detailed description of the preferred embodiment when taken in conjunction with the attached drawings and appended claims.

DETAILED DESCRIPTION

Figure 1:
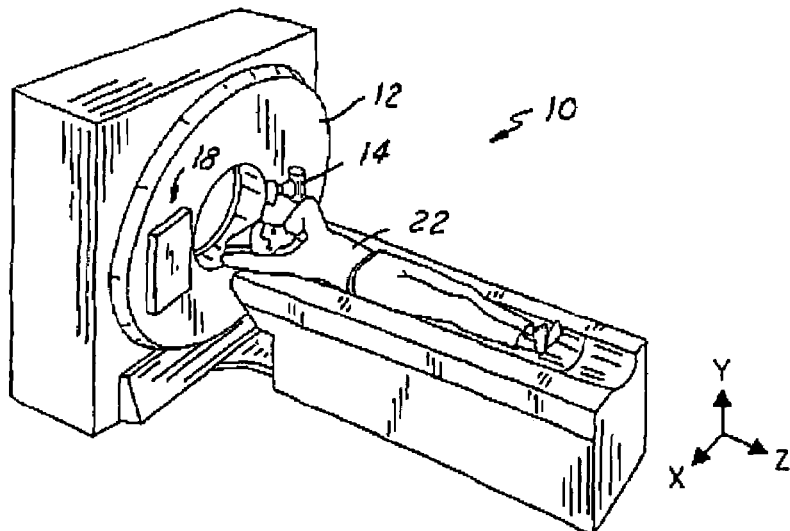
FIG. 1 is an illustration computed tomography imaging system for use in the present invention.
Figure 2:
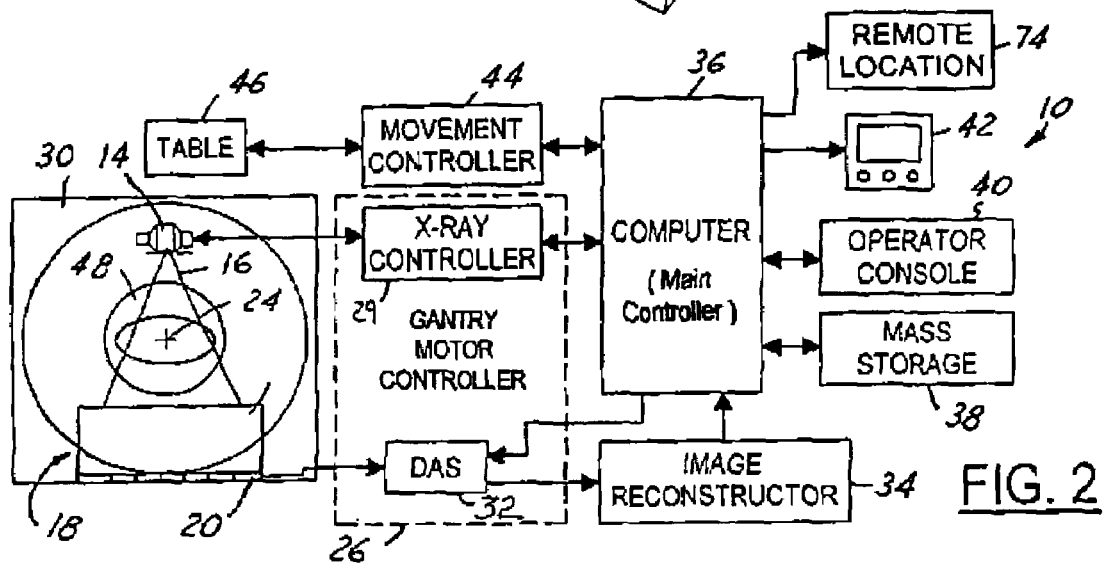
FIG. 2 is a block diagram of the imaging system illustrated in FIG. 1.

Referring now to FIGS. 1 and 2, which are illustrations of a computed tomography (CT) imaging system 10 for use with the detector assembly 18 of the present invention. Although a particular CT imaging system 10 has been illustrated, it should be understood that the detector assembly 18 of the present invention could be utilized in a wide variety of imaging systems. The CT imaging system 10 includes a scanner assembly 12 illustrated as a gantry assembly. The scanner assembly 12 includes an x-ray source 14 for projecting a beam of x-rays 16 toward a detector assembly 18 positioned opposite the x-ray source 14. The detector assembly 18 includes a plurality of detector elements 20 which combine to sense the projected x-rays 16 that pass through an object, such as a medical patient 22. Each of the plurality of detector elements 20 produces an electrical signal that represents the intensity of an impinging x-ray beam and hence the attenuation of the beam 16 as it passes through the object of patient 22. Commonly, during a scan to acquire x-ray projection data, the scanner assembly 12 is rotated about the center of rotation 24. In one embodiment, illustrated in FIG. 2, detector elements 20 are arranged in one row such that projection data corresponding to a single image slice is acquired during a scan. In other embodiments, the detector elements 20 can be arranged in a plurality of parallel rows, such that projection data corresponding to a plurality of parallel slices can be acquired simultaneously during a scan.

The rotation of the scanner assembly 12 and the operation of the x-ray source 14 are preferably governed by a control mechanism 26. The control mechanism 26 preferably includes an x-ray controller 29 that provides power and timing signals to the x-ray source 14 and a scanner motor controller 30 that controls the rotational speed and position of the scanner assembly 12. A data acquisition system (DAS) 32 in control mechanism 26 samples analog data from the detector elements 20, commonly a photodetector array, and converts the data to digital signals for subsequent processing. An image reconstructor 34 receives sampled and digitized x-ray data from DAS 32 and performs high speed image reconstruction. The reconstructed image is applied as an input to a computer 36, or main controller, which stores the image in a mass storage device 38.

The computer 36 also can receive commands and scanning parameters from an operator via console 40 that has a keyboard or similar input device. An associated display 42 allows the operator to observe the reconstructed image and other data from the computer 36. The operator supplied commands and parameters are used by computer 36 to provide control signals and information to the DAS 32, x-ray controller 29, and scanner motor controller 30. In addition, the computer 36 operates a table motor controller 44 which controls a motorized table 46 to position patient 22 within the scanner assembly 12. Particularly, the table 46 moves portions of the patient 22 through the scanner opening 48.

Figure 3:
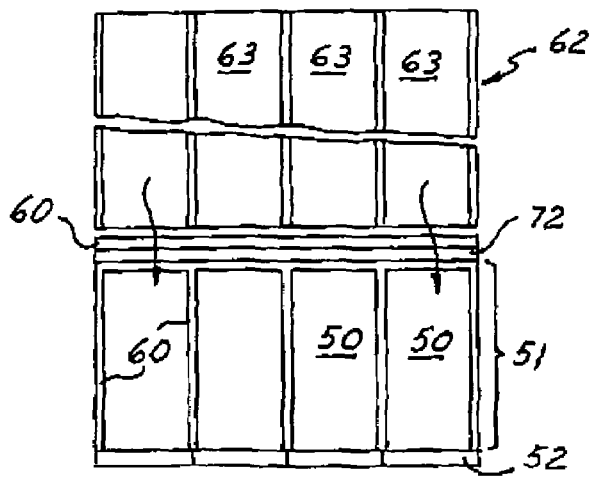
FIG. 3 is an illustration of a detector assembly for use in the imaging system illustrated in FIG. 1.

Each of the detector elements 20 of the detector assembly 18 produces a separate electrical signal that is a measurement of the beam attenuation at the detector location. As illustrated in FIG. 3, the detector assembly 18 includes a plurality of scintillator elements 50, formed as part of a scintillator assembly 51, each of which is associated with one of the detector elements 20. Scintillator elements 50 are known devices that, when struck by x-rays, convert at least a portion of the energy of the x-rays into light that can be detected by the detector elements 20, commonly photodetectors 52. The photodetectors 52, such as photodiodes or photocells, are commonly optically coupled to the backs of the scintillator elements 50 and are utilized to generate electrical signals representative of the light output from the scintillator elements 50. The attenuation measurements from all detector elements 20 in the detector assembly 18 are acquired separately to produce a transmission profile. It should be understood that FIG. 3 illustrates a cross-section of the detector assembly 18 and is intended to be representative of both linear and multi-dimensional arrays of detectors. The imaging system 10 further includes a collimator assembly 62. The collimator assembly 62 is utilized to control the x-rays impacting the scintillator elements 50. The collimator assembly 62 is comprised of a plurality of collimator elements 63, each corresponding to one of the scintillator pack walls 60.

The present invention provides unique field-testing capabilities by including in the detector assembly 18 electroluminescent panel 64 positioned between the collimator assembly 62 and the scintillator assembly 51. Although the electroluminescent panel 64 is illustrated positioned between the collimator assembly 62 and the scintillator assembly 51, it is contemplated that in other embodiments the collimator assembly 62 can be positioned between the electroluminescent panels 64 and the scintillator assembly 51. The electroluminescent panel 64 is preferably mounted in communication with the scintillator assembly 51 and is in communication with the main controller 36. The electroluminescent panel 64 is capable of generating radiation that elicits a response from the detector elements 20. It is contemplated that the radiation generated by the electroluminescent panel 64 may be either exciting or non-exciting radiation. Exciting radiation is radiation designed to excite one of the scintillator elements 50 such that the scintillator element 50 in turn generates light, which can be read by a corresponding detector element 20. Non-exciting radiation is radiation that does not excite the scintillator element 50 but directly elicits a response from a detector element 20. The advantage of the present invention is that the electroluminescent panel 64 can elicit a response from the detector array 18 without the use of x-rays 16. The placement of the electroluminescent panel 64 allows activation of the detector elements 20 even while a patient 22 is positioned within the imaging system 10. In this fashion the present invention allows for testing and monitoring of the detector assembly 18 without x-rays 16, remotely, and without the removal of the patient 22. The electroluminescent panel 64 further acts as a light, dust, and bodily fluid shield thereby protecting the detector assembly 18.

Figure 4:
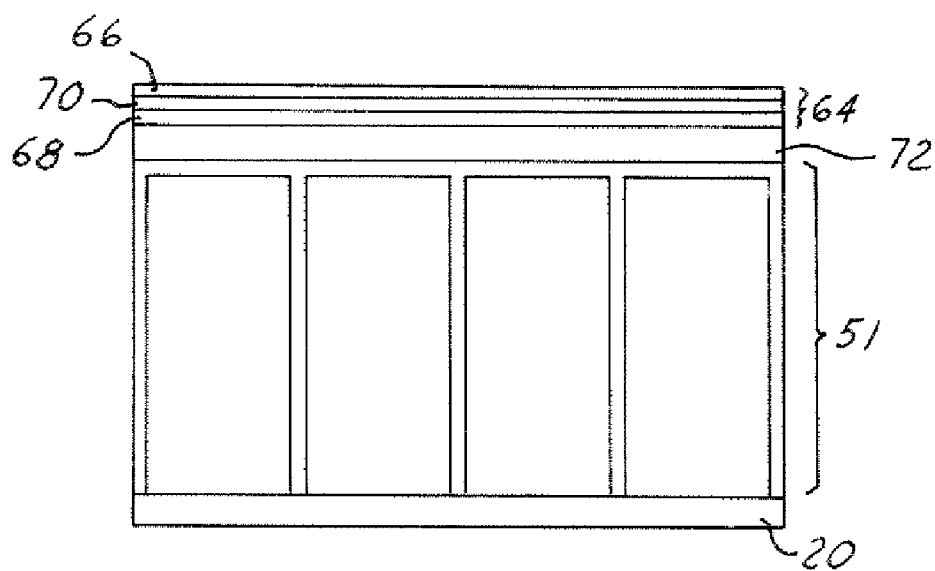
FIG. 4 is a detail illustration of an electroluminescent panel for use in the detector assembly illustrated in FIG. 3.

Although a wide variety of electroluminescent panels 64 are contemplated by the present invention, one embodiment contemplates the use of an electroluminescent panel 64 as illustrated in FIG. 4. The electroluminescent panel 64 is comprised of a first conductor film 66, a second conductor film 68, and an electroluminescent film 70 positioned between the two conductor films 66,68. The second conductor film 68 is preferably transparent. The first conductor film 66 may be either transparent or metallic such that the output of the electroluminescent film 70 is directed towards the scintillator assembly 51.

The present invention can further include a reflective film 72, preferably positioned between the electroluminescent panel 64 and the scintillator assembly 51, that acts to allow the radiation generated by the electroluminescent film 70 to pass through un-attenuated while simultaneously acting to reflect the internally emitted light from the scintillator elements 50 or non-exciting radiation back into the scintillator elements 50 and towards the photodiode 20. Although a variety of reflective films 72 may be utilized, one embodiment contemplates the use of a multi-layer reflective film such as dielectric reflector film. The multi-layer reflective film 72 can be designed as a one-way mirror. In other embodiments, the multi-layer reflective film 72 can be designed with band pass capability wherein the multi-layer reflective film 72 transmits certain wave lengths of light while acting as a reflector for other wavelengths.

Figure 5:
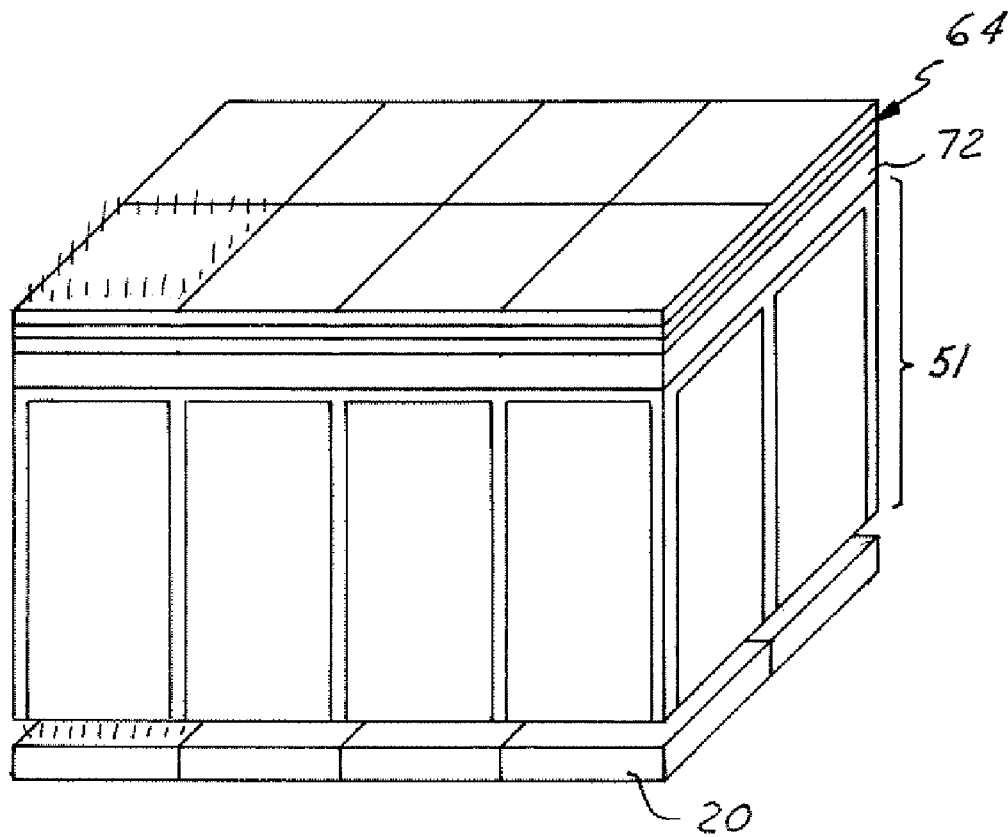
FIG. 5 is an illustration of the detector assembly illustrated in FIG. 3, the detector assembly illustrated testing individual detector cells.
Figure 6:
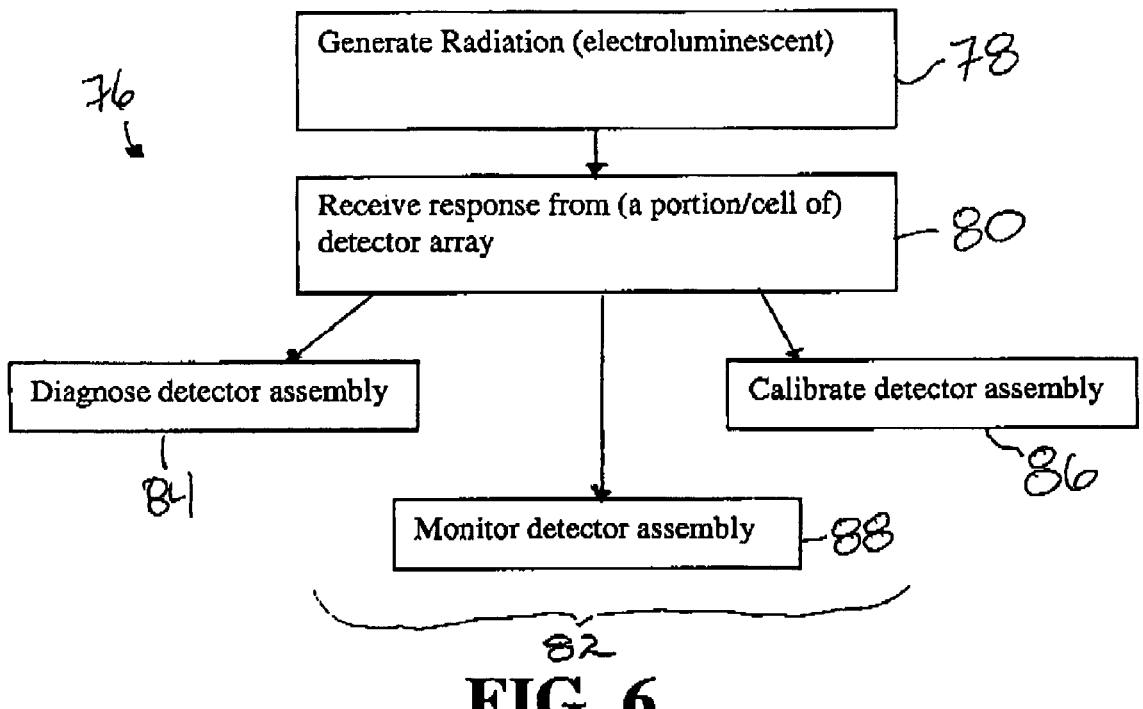
FIG. 6 is an illustration of a logic used in the main controller of the imaging system illustrated in FIG. 1.
Figure 7:
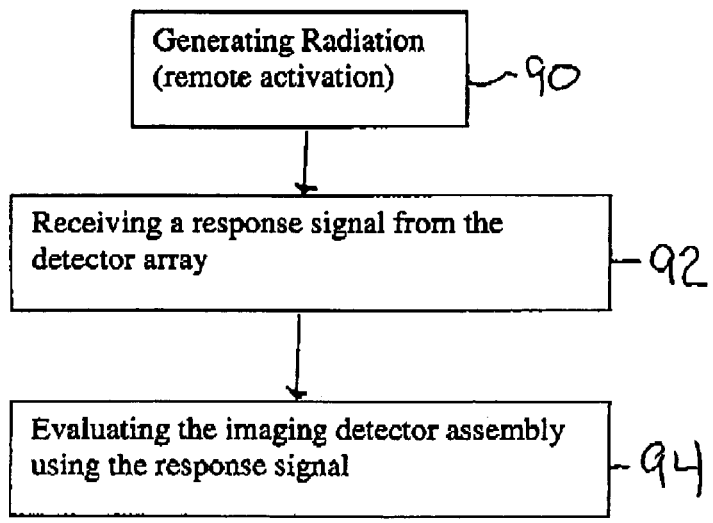
FIG. 7 is an illustration of a methodology incorporated by the logic illustrated in FIG. 6.

The disclosed invention allows for the testing of the entire detector assembly 18, a portion of the detector assembly, or selected detector cells (see FIG. 5). The testing can be implemented anytime during assembly or after final assembly within the factory or for any purpose in the field. The present invention allows for field testing and monitoring of the CT detector assembly 18 without x-rays 16, either on-site or remotely, and without the need for removal of the patient 22. Through the use of a remote connection 74, such as a network connection, in communication with the detector assembly 18, such as through connection with the main controller 36, allows for true remote diagnostics or monitoring. This is especially useful since the remote activation of x-rays 16 is not desirable. The remote diagnostic allows calibration, correction, and monitoring of performance to be done on-site or from a remote site such as the manufacturer's site. A manufacturer or administrator may thereby monitor the performance of the detector assembly 18. Additionally, detector segments or modules can be calibrated without the removal of the patient 16. The main controller 36 preferably contains a logic 76 as illustrated in FIG. 6. The logic 76 is adapted to generate radiation 78 preferably using the electroluminescent panel 64. The logic 76 then receives a response from the detector array 80 and evaluates the response 82. The evaluation 82 may take the form of diagnosing the detector assembly 84, calibrating the detector assembly 86 or monitoring the detector assembly 88. This adapted logic 76 translates to a method illustrated in FIG. 7. The method includes generating radiation 90, receiving a response signal from the detector array 92, and evaluating the imaging detector assembly using the response signal 94. Again, evaluating 94 may be comprised of diagnosing, calibrating, or monitoring. It is also contemplated that the method may include remote activation of the generated radiation and remote evaluation of the imaging detector assembly.

While particular embodiments of the invention have been shown and described, numerous variations and alternative embodiments will occur to those skilled in the art. Accordingly, it is intended that the invention be limited only in terms of the appended claims.

The invention claimed is:

1. An imaging assembly comprising:
   an x-ray source;
   a controller in communication with said x-ray source:
   a detector assembly in communication with said controller, said detector assembly comprising:
   a detector array in communication with said controller;
   a scintillator assembly positioned between said detector array and said x-ray source;
   a collimator assembly positioned in between said scintillator assembly and said x-ray source; and
   an electroluminescent panel in communication with said scintillator assembly, said electroluminescent panel in communication with said controller, said electroluminescent panel having an active condition wherein said electroluminescent panel generates radiation eliciting a response from said detector array, said electroluminescent panel generating radiation without receiving x-rays.

2. An imaging assembly as described in claim 1, further comprising:
   a reflector film in communication with said electroluminescent panel, said reflector film positioned between said electroluminescent panel and said scintillator, said reflector film allowing said radiation to pass through while reflecting light generated by said scintillator assembly.

3. An imaging assembly as described in claim 2, wherein said reflector film comprises dielectric reflector film allowing said radiation to pass into said scintillator, said dielectric reflector film preventing said radiation from passing out of said scintillator.

4. An imaging assembly as described in claim 1, wherein said electroluminescent panel generates non-exciting radiation.

5. An imaging assembly as described in claim 1, wherein said electroluminescent panel generates exciting radiation.

6. An imaging assembly as described in claim 1, wherein said controller comprises:
   a logic adapted to:
   generate said radiation using said electroluminescent panel;
   receive said response from said detector array; and
   diagnose said detector assembly using said response.

7. An imaging assembly as described in claim 1, wherein said controller comprises:
   a logic adapted to:
   generate said radiation using said electroluminescent panel;
   receive said response from said detector array; and
   calibrate said detector assembly using said response.

8. An imaging assembly as described in claim 1, wherein said controller comprises:
   a logic adapted to:
   generate said radiation using said electroluminescent panel;
   receive said response from said detector array; and
   monitor said detector assembly using said response.

9. An imaging assembly as described in claim 1, wherein said controller comprises:
   a logic adapted to:
   test only a portion of said detector assembly by way of eliciting a response from only a portion said detector array.

10. An imaging assembly as described in claim 9, wherein said portion comprises a selected cell.

11. An imaging assembly as described in claim 2, wherein said dielectric reflector film comprises a multi-layer band pass film.

12. An imaging assembly as described in claim 2, wherein said dielectric reflector film comprises a one-way mirror film.

13. An imaging detector assembly comprising:
    a controller:
    a detector assembly in communication with said controller, said detector assembly comprising:
    a photodetector array in communication with said controller;
    a collimator assembly;
    a scintillator assembly; positioned between said photodetector array and said collimator assembly; and
    an electroluminescent panel positioned between said collimator assembly and said scintillator assembly, said electroluminescent panel in communication with said controller, said electroluminescent panel having an active condition wherein said electroluminescent panel generates radiation eliciting a response from said detector array, said electroluminescent panel generating radiation without receiving x-rays.

14. An imaging assembly as described in claim 13, further comprising:
    a reflector film in communication with said electroluminescent panel, said reflector film positioned between said electroluminescent panel and said scintillator, said reflector film allowing said radiation to pass through while reflecting light generated by said scintillator assembly.

15. An imaging detector assembly as described in claim 13, wherein said electroluminescent panel comprises:
    a first conductive film;
    a second conductive film; and
    a electro luminescent film between said first conductive film and said second conductive film.

16. An imaging detector assembly as described in claim 15, wherein said first conductive film comprises a transparent conductor.

17. An imaging detector assembly as described in claim 15, wherein said first conductive film comprises a metallic conductor.

18. A method of testing an imaging detector assembly comprising:

generating radiation from an electroluminescent panel positioned in communication with a scintillator assembly, said radiation exciting said scintillator assembly;

receiving a response signal from a detector array, said response signal generated by said detector array in response to said radiation; and evaluating the imaging detector assembly using said response signal.

19. A method of testing an imaging detector assembly as described in claim 18, wherein said evaluating said imaging detector assembly comprises:

diagnosing said imaging detector assembly.

20. A method of testing an imaging detector assembly as described in claim 18, wherein said evaluating said imaging detector assembly comprises:

calibrating said imaging detector assembly.

21. A method of testing an imaging detector assembly as described in claim 18, further comprising:

activating said electroluminescent panel from a off-site location; and evaluating said imaging detector assembly from said off site location.

\* \* \* \* \*